(12) United States Patent
Rasmussen et al.

(10) Patent No.: US 8,972,005 B2
(45) Date of Patent: Mar. 3, 2015

(54) SUBTHRESHOLD LEAD IMPEDANCE MEASUREMENT FOR SUBCUTANEOUS DEVICE

(71) Applicant: Medtronic, Inc., Minneapolis, MN (US)

(72) Inventors: Marshall J. Rasmussen, Mesa, AZ (US); Forrest C. M. Pape, New Brighton, MN (US); Lonny V. Cabelka, San Clemente, CA (US)

(73) Assignee: Medtronic, Inc., Minneapolis, MN (US)

( * ) Notice: Subject to any disclaimer, the term of this patent is extended or adjusted under 35 U.S.C. 154(b) by 29 days.

(21) Appl. No.: 13/795,471

(22) Filed: Mar. 12, 2013

(65) Prior Publication Data

US 2014/0277285 A1    Sep. 18, 2014

(51) Int. Cl.
| | | |
|---|---|---|
| *A61N 1/20* | (2006.01) | |
| *A61N 1/378* | (2006.01) | |
| *A61N 1/39* | (2006.01) | |
| *A61N 1/37* | (2006.01) | |
| *A61N 1/362* | (2006.01) | |

(52) U.S. Cl.
CPC ............... *A61N 1/378* (2013.01); *A61N 1/3912* (2013.01); *A61N 1/3706* (2013.01); *A61N 1/3625* (2013.01)
USPC .......................................................... 607/9

(58) Field of Classification Search
USPC ........................................................ 607/8–9
See application file for complete search history.

(56) References Cited

U.S. PATENT DOCUMENTS

| | | | |
|---|---|---|---|
| 4,140,131 A | 2/1979 | Dutcher et al. | |
| 4,180,078 A | 12/1979 | Anderson | |
| 4,949,720 A | 8/1990 | Thompson | |
| 5,163,427 A | 11/1992 | Keimel | |
| 5,188,105 A | 2/1993 | Keimel | |
| 5,201,865 A | 4/1993 | Kuehn | |
| 5,470,341 A | 11/1995 | Kuehn et al. | |
| 5,470,345 A | 11/1995 | Hassler et al. | |
| 5,527,346 A | 6/1996 | Kroll | |
| 5,683,432 A | 11/1997 | Goedeke et al. | |
| 5,755,742 A | 5/1998 | Schuelke et al. | |
| 6,016,445 A | 1/2000 | Baura | |
| 6,317,628 B1 | 11/2001 | Linder et al. | |
| 6,512,940 B1 | 1/2003 | Brabec et al. | |
| 6,522,915 B1 | 2/2003 | Ceballos et al. | |
| 6,620,186 B2 | 9/2003 | Saphon et al. | |
| 6,622,046 B2 | 9/2003 | Fraley et al. | |
| 6,963,773 B2 | 11/2005 | Waltman et al. | |
| 7,647,095 B2 | 1/2010 | Bhunia | |
| 7,877,139 B2 | 1/2011 | Ostroff | |
| 8,155,740 B2 | 4/2012 | Wanasek | |
| 8,209,005 B1 | 6/2012 | Moulder et al. | |
| 2004/0044371 A1 | 3/2004 | Tamura et al. | |
| 2007/0203553 A1 | 8/2007 | Smits | |
| 2010/0324618 A1* | 12/2010 | Wanasek | 607/9 |

* cited by examiner

*Primary Examiner* — Carl H Layno
*Assistant Examiner* — Jon Eric C Morales
(74) *Attorney, Agent, or Firm* — Evans M. Mburu (57) ABSTRACT

A subthreshold lead impedance technique is described for an implantable medical device. The lead impedance technique may be applicable to a subcutaneous implantable cardioversion defibrillator device and utilizes an output circuit of the device coupled between a first diode and a second diode to define a current path through two electrodes coupled to the output circuit. The second diode is further coupled to a switch to provide a current pathway from the first diode to circuit ground. A control circuit is coupled to the output circuit, the first diode, the second diode, and the switch to bias a leg of the output circuit in a conducting state while biasing the other legs of the output circuit in a non-conducting state.

20 Claims, 4 Drawing Sheets

(12) United States Patent

SUBTHRESHOLD LEAD IMPEDANCE MEASUREMENT FOR SUBCUTANEOUS DEVICE

FIELD

The present disclosure relates to body implantable medical devices and, more particularly to circuits and techniques for measuring lead impedance of an implantable medical device.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with implantable medical devices.

Implantable medical electrical leads are used with a wide variety of these implantable medical devices. For example, in the field of cardiac stimulation and monitoring, implantable leads are used with an implantable pulse generator (IPG), or implantable cardioverter/defibrillator (ICD), or a subcutaneous implantable cardioverter defibrillator (SubQ ICD). Implantable medical leads may be configured to allow electrodes to be positioned at desired cardiac locations so that the device can monitor and/or deliver stimulation therapy to the desired locations.

Implantable medical leads are also used with other types of therapy delivery devices to provide, as examples, neurostimulation, muscular stimulation, or gastric stimulation to target patient tissue locations via electrodes on the leads and located within or proximate to the target tissue. As one example, implantable leads may be positioned proximate to the vagal nerve for delivery of neurostimulation to the vagal nerve. Additionally, implantable leads may be used by medical devices for patient sensing and, in some cases, for both sensing and stimulation. For example, electrodes on implantable leads may detect electrical signals within a patient, such as an electrocardiogram, in addition to delivering electrical stimulation.

Currently, ICD's use endocardial or epicardial leads which extend from the ICD housing through the venous system to the heart. Electrodes positioned in or adjacent to the heart by the leads are used for pacing and sensing functions. Cardioversion and defibrillation shocks are generally applied between a coil electrode carried by one of the leads and the ICD housing, which acts as an active can electrode.

A SubQ ICD differs from the more commonly used ICD's in that the housing and leads are typically implanted subcutaneously such that the sensing and therapy are accomplished subcutaneously. The SubQ ICD does not require leads to be placed in the bloodstream. Instead, the SubQ ICD makes use of one or more electrodes on the housing, together with a subcutaneous lead that carries a defibrillation coil electrode and a sensing electrode.

The absence of endocardial or epicardial electrodes presents a challenge to determining a lead fault of the SubQ ICD. As described herein, the present disclosure addresses the need in art to provide mechanisms for performing a lead impedance measurement for a SubQ ICD.

SUMMARY

A lead impedance system for an implantable medical device (IMD), such as a subcutaneous implantable cardioverter defibrillator (SubQ ICD), is disclosed. The lead impedance system for the IMD is performed through delivery of a minimum energy signal through a first and a second electrode coupled to the IMD.

In an embodiment, the IMD includes a lead coupled to a housing with the lead carrying the first electrode. The second electrode may be coupled to the housing. The housing includes operational circuitry having a control circuit and an output circuit that is coupled to the first electrode and the second electrode. The output circuit is arrayed in the form of four interconnected legs. The four interconnected legs are configured having a first leg and a third leg defining the output circuit high side and a second leg and a fourth leg defining the output circuit low side. The control circuit is configured to bias the four interconnected legs in one of a conducting or non-conducting state.

In an embodiment, the operational circuitry further includes a first diode coupled to the first leg and an impedance testing leg coupled to the second electrode. The control circuit is configured to bias the first leg in a conducting state and to bias the second, third and fourth legs in a non-conducting state during a lead impedance measurement.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is illustrative in nature and is not intended to limit the embodiments of the disclosure or the application and uses of such embodiments. Furthermore, there is no intention to be bound by any expressed or implied theory presented in the preceding technical field, background, brief summary or the following detailed description.

In the present disclosure, the inventors have disclosed circuits and techniques associated with generating therapy stimulation energy having varying waveforms for the delivery of therapies such as pacing, defibrillation and cardioversion by an implantable medical device. The configurable waveforms of the therapy stimulation generated in accordance with aspects of this disclosure include a ramped or stepped leading edge that mimics the cell response behavior for a given patient. However, the disclosure is not limited to these specific waveforms, but rather is applicable to any type of waveform. The waveforms reduce the thresholds required to achieve capture, thereby increasing the efficiency and effectiveness of the implantable medical therapies.

Figure 1:
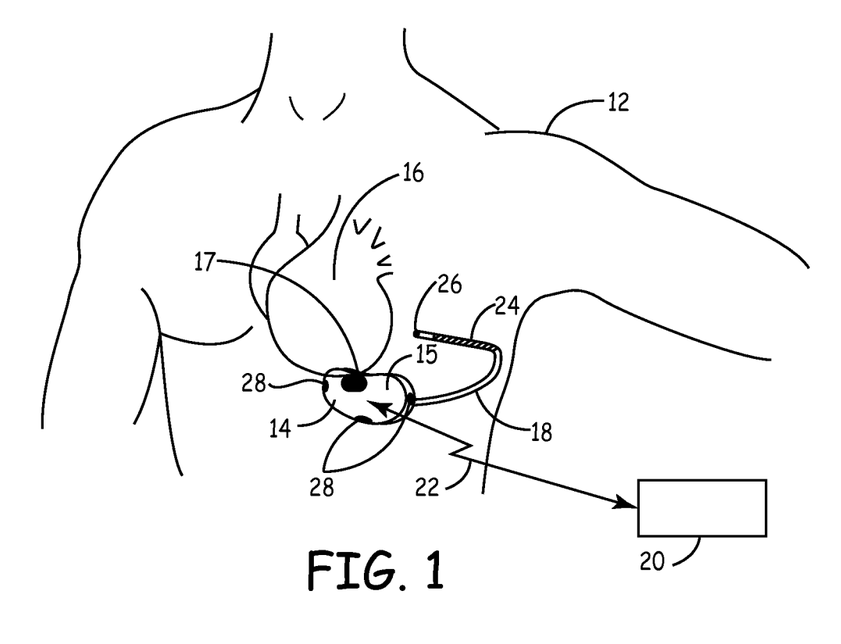
FIG. 1 is a schematic diagram of an implantable medical device.

FIG. 1 is a schematic diagram of an exemplary medical device in which the present disclosure may be usefully practiced. As illustrated in FIG. 1, the present disclosure may be utilized in an implantable medical device (IMD) 14 that includes a housing 15 containing circuitry for operating IMD 14 that is subcutaneously implanted in a patient, outside the ribcage of patient 12, anterior to the cardiac notch, for example. According to an embodiment, housing 15 may be implanted in the pectoral region of the patient 12. Further, IMD 14 may include a subcutaneous sensing and cardioversion/defibrillation therapy delivery lead 18 coupled to the IMD 14 that is tunneled subcutaneously into a location adjacent to a portion of a latissimus dorsi muscle of patient 12. Specifically, lead 18 is tunneled subcutaneously from the median implant pocket of IMD 14 laterally and posterially to the patient's back to a location opposite the heart such that the heart 16 is disposed between the IMD 14 and the distal electrode coil 24 and distal sensing electrode 26 of lead 18.

It is understood that while the subcutaneous IMD 14 is shown positioned through loose connective tissue between the skin and muscle layer of the patient, the term "subcutaneous device" is intended to include a device that can be positioned in the patient to be implanted using any non-intravenous location of the patient, such as below the muscle layer or within the thoracic cavity, for example.

Further referring to FIG. 1, programmer 20 is shown in telemetric communication with IMD 14 by wireless communication link 22. Communication link 22 may be any appropriate wireless link such as Bluetooth, NFC, WiFi, MICS, or as described in U.S. Pat. No. 5,683,432 "Adaptive Performance-Optimizing Communication System for Communicating with an Implantable Medical Device" to Goedeke, et al.

IMD 14 may be constructed from stainless steel, titanium or ceramic as described in U.S. Pat. No. 4,180,078 "Lead Connector for a Body Implantable Stimulator" to Anderson and U.S. Pat. No. 5,470,345 "Implantable Medical Device with Multi-layered Ceramic Enclosure" to Hassler, et al. The electronics circuitry of IMD 14 may be incorporated on a polyamide flex circuit, printed circuit board (PCB), ceramic substrate with integrated circuits packaged in leadless chip carriers, chip scale packaging, and/or wafer scale packaging.

Lead 18, which is inserted within a connector (not shown) positioned on housing 15 to electrically couple the lead to the circuitry located in housing 15, includes a distal defibrillation coil electrode 24, a distal sensing electrode 26, an insulated flexible lead body and a proximal connector pin (not shown) for connection to housing 15 via the connector. In some embodiments, distal sensing electrode 26 may be sized appropriately to match the sensing impedance of one or more electrodes 28a, 28b (collectively "28") that are positioned along housing 15 to form a housing-based subcutaneous electrode array with electrodes 28 positioned to form orthogonal signal vectors.

IMD 14 in an embodiment of the present disclosure includes miniaturized circuitry for providing therapy, as described in detail below. In some embodiments, an optical hemodynamic sensor 17 such as a multiple waveform oximeter, or a mixed-venous oxygen sensor may be included. Electrodes 28 and optical sensor 17 are welded into place on the outer surface of the housing 15 and are connected via wires (not shown) to operational circuitry (described herein below) located inside housing 15. Electrodes 28 may be constructed of flat plates, or alternatively, spiral electrodes as described in U.S. Pat. No. 6,512,940 "Subcutaneous Spiral Electrode for Sensing Electrical Signals of the Heart" to Brabec, et al., and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al.

The operational circuitry employed in IMD 14 can take any of the known forms that detect a tachyarrhythmia from the sensed ECG and provide cardioversion/defibrillation shocks as well as post-shock pacing as needed while the heart recovers. An exemplary simplified block diagram of such circuitry adapted to function employing the first and second cardioversion-defibrillation electrodes as well as the ECG sensing and pacing electrodes described herein below is set forth in U.S. Pat. No. 7,647,095, "Method and Apparatus for Verifying a Determined Cardiac Event in a Medical Device Based on Detected Variation in Hemodynamic Status" to Bhunia incorporated herein by reference in its entirety. It will be understood that the simplified block diagram does not show all of the conventional components and circuitry of such devices including digital clocks and clock lines, low voltage power supply and supply lines for powering the circuits and providing pacing pulses or telemetry circuits for telemetry transmissions between the IMD 14 and external programmer 20.

Figure 2:
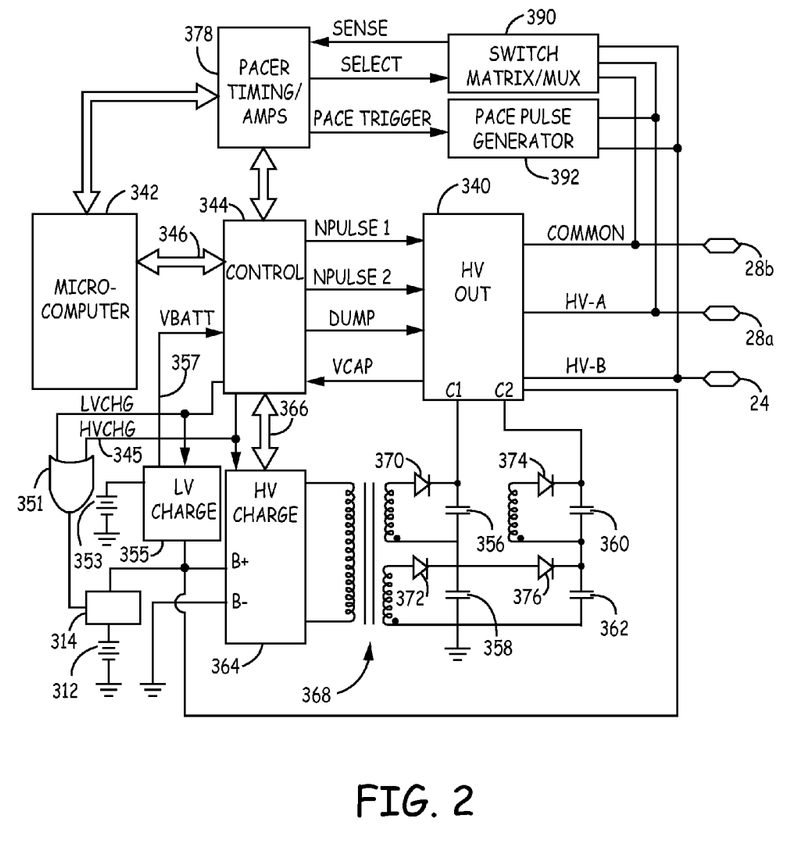
FIG. 2 is a schematic diagram of operational circuitry included in an embodiment of an implantable medical device.

FIG. 2 is a schematic diagram of operational circuitry included in a medical device according to an embodiment of the present disclosure. It is understood that although the system of FIG. 2 includes both low and high power therapy, the present disclosure may be employed in a device that provides only one therapy, such as a high power defibrillation therapy, for example. Accordingly, some embodiments of the disclosure are contemplated without the components in FIG. 2 that are associated with low voltage therapy, such as pacing stimulation.

As illustrated in FIG. 2, the operational circuitry is provided with one or more energy sources. The energy source may be provided in any suitable manner. For example, the energy source may be programmable or static, the energy source may be provided by one or more batteries, the energy source may be a switched or linear regulated source, etc. In an embodiment, a low voltage battery 353 supplies power to the circuitry and the pacing output capacitors to supply pacing energy in a manner well known in the art. The low voltage battery may include one or two conventional LiCFx, LiMnO2 or LiI2 cells, for example, and a high voltage battery 312 may include one or two conventional LiSVO or LiMnO2 cell. In the embodiment, a high voltage battery 340 may also be included to provide energy for high power therapies, such as cardioversion/defibrillation.

In FIG. 2, ICD functions are controlled by means of stored software, firmware and hardware that cooperatively monitor the EGM, determine when a cardioversion-defibrillation shock or pacing is necessary, and deliver prescribed cardioversion-defibrillation and pacing therapies. The schematic diagram of FIG. 2 incorporates circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, for example, both incorporated herein by reference in their entireties, for selectively delivering single phase, simultaneous biphasic and sequential biphasic cardioversion-defibrillation shocks typically employing an ICD IPG housing electrode coupled to the COMMON output 28b of high voltage output circuit 340 and one or two cardioversion-defibrillation electrodes disposed posteriorly and subcutaneously and coupled to the HV-A and HV-B outputs (28a and 24, respectively) of the high voltage output circuit 340. The circuitry of the SubQ ICD 14 of the present disclosure can be made simpler by adoption of one such cardioversion-defibrillation shock waveform for delivery simply between the first and second cardioversion-defibrillation electrodes 28a and 24 coupled to the HV-A and HV-B outputs respectively. Alternatively, the third cardioversion-defibrillation electrode 28b can be coupled to the COMMON output as depicted in FIG. 2 and the first and second cardioversion-defibrillation electrodes 28a and 24 can be electrically connected in to the HV-A and the HV-B outputs, respectively, as depicted in FIG. 2.

The cardioversion-defibrillation shock energy and capacitor charge voltages can be intermediate to those supplied by ICDs having at least one cardioversion-defibrillation electrode in contact with the heart and most AEDs having cardioversion-defibrillation electrodes in contact with the skin. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the waveform used. The SubQ ICD of the present disclosure uses maximum voltages in the range of about 700 to about 3150 Volts and is associated with energies of about 25 Joules to about 210 Joules. The total high voltage capacitance could range from about 50 to about 300 microfarads.

Such cardioversion-defibrillation shocks are only delivered when a malignant tachyarrhythmia, e.g., ventricular fibrillation is detected through processing of the far field cardiac ECG employing one of the available detection algorithms known in the ICD art.

In FIG. 2, pacer timing/sense amplifier circuit 378 processes the far field ECG SENSE signal that is developed across a particular ECG sense vector defined by a selected pair of the electrodes 28a, 24, and optionally, electrode 28b if present as noted above. The selection of the sensing electrode pair is made through the switch matrix/MUX 390 in a manner to provide the most reliable sensing of the EGM signal of interest, which would be the R wave for patients who are believed to be at risk of ventricular fibrillation leading to sudden death. The far field ECG signals are passed through the switch matrix/MUX 390 to the input of a sense amplifier in the pacer timing/sense amplifier circuit 378. Bradycardia is typically determined by an escape interval timer within the pacer timing circuit 378 or the timing and control circuit 344, and pacing pulses that develop a PACE TRIGGER signal applied to the pacing pulse generator 392 when the interval between successive R-waves exceeds the escape interval. Bradycardia pacing is often temporarily provided to maintain cardiac output after delivery of a cardioversion-defibrillation shock that may cause the heart to slowly beat as it recovers function.

Detection of a malignant tachyarrhythmia is determined in the timing and control circuit 344 as a function of the intervals between R-wave sense event signals that are output from the pacer timing/sense amplifier circuit 378 to the timing and control circuit 344. Certain steps in the performance of the detection algorithm criteria are cooperatively performed in a microcomputer 342, including stored detection criteria that may be programmed into via a telemetry interface (not shown) conventional in the art.

The microcomputer 342 is generally representative of a processor and associated memory. The memory, for example, may include computer readable instructions that, when executed by processor, cause the operational circuitry and or any other component of the medical device to perform various functions attributed to them. For example, the memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. The processor, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions attributed to the microcomputer 342 may be embodied as software, firmware, hardware, or any combination thereof.

Data and commands are exchanged between microcomputer 342 and timing and control circuit 344, pacer timing/amplifier circuit 378, and high voltage output circuit 340 via a bi-directional data/control bus 346. The pacer timing/amplifier circuit 378 and the timing and control circuit 344 are clocked at a slow clock rate. The microcomputer 342 is normally asleep, but is awakened and operated by a fast clock by interrupts developed by each it-wave sense event or on receipt of a downlink telemetry programming instruction or upon delivery of cardiac pacing pulses to perform any necessary mathematical calculations, to perform tachycardia and fibrillation detection procedures, and to update the time intervals monitored and controlled by the timers in pace/sense circuitry 378.

The detection algorithms are highly sensitive and specific for the presence or absence of life threatening ventricular arrhythmias, e.g., ventricular tachycardia (V-TACH) and ventricular fibrillation (V-FIB). Detection can be provided via R-R Cycle length instability detection algorithms. In addition, detection algorithms for atrial fibrillation may also be included.

Although the ICD of the present disclosure may rarely be used for an actual sudden death event, the simplicity of design and implementation allows it to be employed in large populations of patients at modest risk with modest cost by medical personnel other than electrophysiologists. Consequently, the ICD of the present disclosure includes the automatic detection and therapy of the most malignant rhythm disorders.

When a malignant tachycardia is detected, high voltage capacitors 356, 358, 360, and 362 are charged to a pre-programmed voltage level by a high-voltage charging circuit 364. The illustration of the embodiment having four capacitors 356, 358, 360, and 362, is merely exemplary. Rather, alternative embodiments may include fewer or more capacitors. It is generally considered inefficient to maintain a constant charge on the high voltage output capacitors 356, 358, 360, 362. Instead, charging is initiated when control circuit 344 issues a high voltage charge command HVCHG delivered on line 345 to high voltage charge circuit 364 and charging is controlled by means of bi-directional control/data bus 366 and a feedback signal VCAP from the HV output circuit 340. High voltage output capacitors 356, 358, 360 and 362 may be of film, aluminum electrolytic or wet tantalum construction.

The negative terminal of high voltage battery 312 is directly coupled to system ground. Switch circuit 314 is normally open so that the positive terminal of high voltage battery 312 is disconnected from the positive power input of the high voltage charge circuit 364. The high voltage charge command HVCHG is also conducted via conductor 349 to the control input of switch circuit 314, and switch circuit 314 closes in response to connect positive high voltage battery voltage EXT B+ to the positive power input of high voltage charge circuit 364. Switch circuit 314 may be, for example, a field effect transistor (FET) with its source-to-drain path interrupting the EXT B+ conductor 318 and its gate receiving the HVCHG signal on conductor 345. High voltage charge circuit 364 is thereby rendered ready to begin charging the high voltage output capacitors 356, 358, 360, and 362 with charging current from high voltage battery 312.

High voltage output capacitors 356, 358, 360, and 362 may be charged to very high voltages, e.g., 700-3150V, to be discharged through the body and heart between the selected electrode pairs among first, second, and, optionally, third subcutaneous cardioversion-defibrillation electrodes 28a, 24, and 28b. The details of the voltage charging circuitry are also not deemed to be critical with regard to practicing the present disclosure; one high voltage charging circuit believed to be suitable for the purposes of the present disclosure is disclosed. High voltage capacitors 356, 358, 360, and 362 are charged by high voltage charge circuit 364 and a high frequency, high-voltage transformer 368. Proper charging polarities are maintained by diodes 370, 372, 374 and 376 interconnecting the output windings of high-voltage transformer 368 and the capacitors 356, 358, 360, and 362. As noted above, the state of capacitor charge is monitored by circuitry within the high voltage output circuit 340 that provides a VCAP, feedback signal indicative of the voltage to the timing and control circuit 344. Timing and control circuit 344 terminates the high voltage charge command HVCHG when the VCAP signal matches the programmed capacitor output voltage, i.e., the cardioversion-defibrillation peak shock voltage.

Timing and control circuit 344 then develops first and second control signals NPULSE 1 and NPULSE 2, respectively, that are applied to the high voltage output circuit 340 for triggering the delivery of cardioverting or defibrillating shocks. The NPULSE 1 signals and NPULSE 2 signals may be provided sequentially, simultaneously or individually. In this way, control circuitry 344 serves to control operation of the high voltage output stage 340, which delivers high energy cardioversion-defibrillation shocks between a selected pair or pairs of the first, second, and, optionally, the third cardioversion-defibrillation electrodes 28a, 24 coupled to the HV-A, HV-B and optionally to the COMMON output 28b as shown in FIG. 2.

Thus, ICD 10 monitors the patient's cardiac status and initiates the delivery of a cardioversion-defibrillation shock through a selected pair or pairs of the first, second and third cardioversion-defibrillation electrodes 28a and 24 in response to detection of a tachyarrhythmia requiring cardioversion-defibrillation. The high HVCHG signal causes the high voltage battery 312 to be connected through the switch circuit 314 with the high voltage charge circuit 364 and the charging of output capacitors 356, 358, 360, and 362 to commence. Charging continues until the programmed charge voltage is reflected by the VCAP signal, at which point control and timing circuit 344 sets the HVCHG signal low terminating charging and opening switch circuit 314. Typically, the charging cycle takes only fifteen to twenty seconds, and occurs very infrequently. The ICD 10 can be programmed to attempt to deliver cardioversion shocks to the heart in the manners described above in timed synchrony with a detected R-wave or can be programmed or fabricated to deliver defibrillation shocks to the heart in the manners described above without attempting to synchronize the delivery to a detected R-wave. Episode data related to the detection of the tachyarrhythmia and delivery of the cardioversion-defibrillation shock can be stored in RAM for uplink telemetry transmission to an external programmer as is well known in the art to facilitate in diagnosis of the patient's cardiac state Housing 14 may include telemetry circuit (not shown in FIG. 2), so that it is capable of being programmed by means of external programmer 20 via a 2-way telemetry link 22 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Programmers and telemetry systems suitable for use in the practice of the present disclosure have been well known for many years. Known programmers typically communicate with an implanted device via a bi-directional radio-frequency telemetry link, so that the programmer can transmit control commands and operational parameter values to be received by the implanted device, and so that the implanted device can communicate diagnostic and operational data to the programmer.

As mentioned above, the output circuit 340 performs several functions. One of those is to monitor the state of capacitor charge of the high voltage output capacitors. Another function is to allow the controlled transfer of energy from the high voltage output capacitors to the patient. In accordance with the present disclosure, another function of the output circuit is to perform lead impedance measurement as will be described below.

Figure 3:
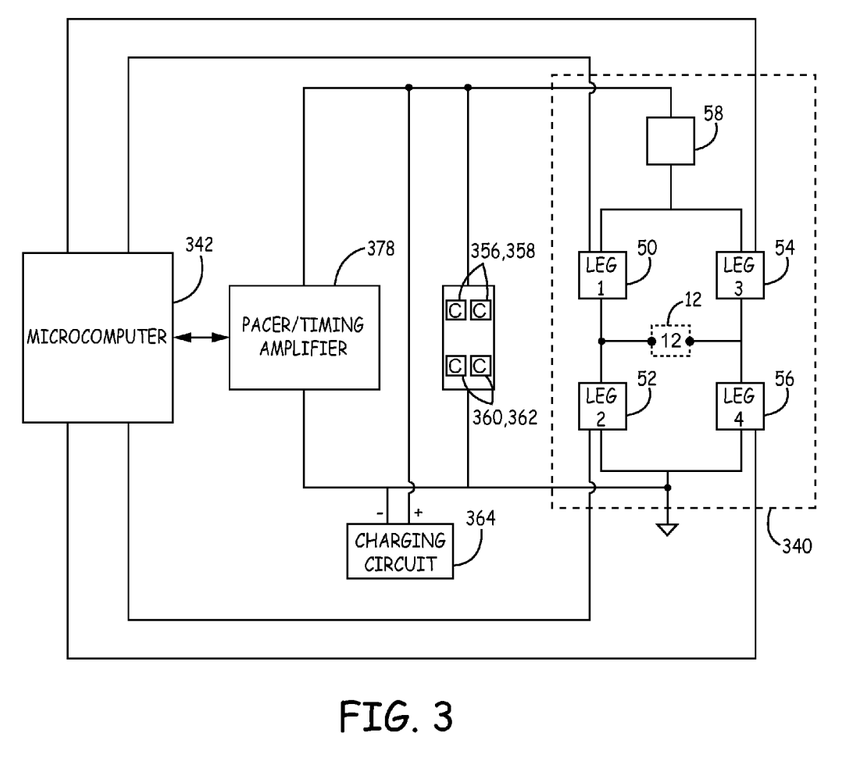
FIG. 3 illustrates an exemplary circuit schematic showing a portion of the operational circuitry of the implantable medical device in accordance with an embodiment of the disclosure.

FIG. 3 illustrates an exemplary schematic showing a portion of the operational circuitry of FIG. 2, in accordance with an embodiment of the disclosure, in greater detail. The output circuit 340 allows the controlled transfer of energy from the energy storage capacitors 356, 358, 360, and 362 to the patient 12.

The output circuit 340 includes four legs 50, 52, 54, and 56 that are interconnected. The interconnection of the four legs with legs 50 and 52 being configured in a parallel orientation alongside legs 54 and 56 and a bridge being provided to intersect each of the pair of parallel connected legs. As is shown in FIG. 3, the interconnected legs are arrayed to define a configuration includes a high side and a low side that may resemble a "H". In other words, the four interconnected legs are arrayed having legs 50 and 54 defining the high side and legs 52 and 56 defining the low side.

The intersecting bridge includes HV-A and HV-B terminals that couple the output circuit 340 to the cardioversion electrodes 24 and 28a. As previously described, patient 12 is connectable (e.g., using leads/electrodes 24, 28a and any other suitable connections) between terminal HV-A located between the switch 50 and switch 52 and terminal HV-B located between switch 54 and switch 56.

Legs 50 and 54 are coupled through a discharge switch 58 to a positive terminal of the energy storage capacitors 356, 358, 360, and 362. The discharge switch 58 may be an insulated gate bipolar transistors (IGBT). Discharge switch 58 is controlled by the timing and control circuit 344 to close and remain in the conducting state during discharge of the capacitors. Leg 52 and 56 are coupled to a negative terminal of the energy storage capacitors 356, 358, 360, and 362. The selection of one or more of the switches 50, 52, 54, 56 under control of control circuit 344 may be used to provide one or more functions. For example, selection of certain switches in one or more configurations may be used to provide one or more types of stimulation pulses, or may be used to provide active or passive recharge, etc.

For example, in accordance with an embodiment, the IMD 14 provides a biphasic defibrillation pulse to the patient in the following manner. With reference to FIG. 3, once the energy storage capacitors 356, 358, 360, and 362 are charged to a selected energy level, the switches 50, 56, and 58 are closed so as to provide a path from the capacitors to electrode 28, 24 for the application of a first phase of a defibrillation pulse to the patient 12. The stored energy travels from the positive terminal of the capacitors, through switch 50, across the patient 12, back through switch 56 to the negative terminal of the capacitors. The first phase of the biphasic pulse therefore applies a positive pulse from the electrode 28 to the electrode 24.

Before the energy storage capacitors 356, 358, 360, and 362 are completely discharged, switch 56 is biased off, by opening switch 58, in preparation for application of the second phase of the biphasic pulse. Once switch 56 is biased off, switch 50 will also become non-conducting because the current flowing through it falls to below its holding current.

After the end of the first phase of the biphasic defibrillation pulse, the switches 58, 54 and 52 are switched on to start the second phase of the biphasic pulse. Switches 54 and 52 provide a path to apply a negative defibrillation pulse to the patient 12. With reference to FIG. 3, the energy travels from the positive terminal of the capacitors 356, 358, 360, and 362, through switch 54, across the electrodes 24, 28 coupled to the patient 12, and out through switch 52 to the negative terminal of the capacitors 356, 358, 360, and 362. The polarity of the second phase of the defibrillation pulse is therefore opposite in polarity to the first phase of the pulse.

Figure 4:
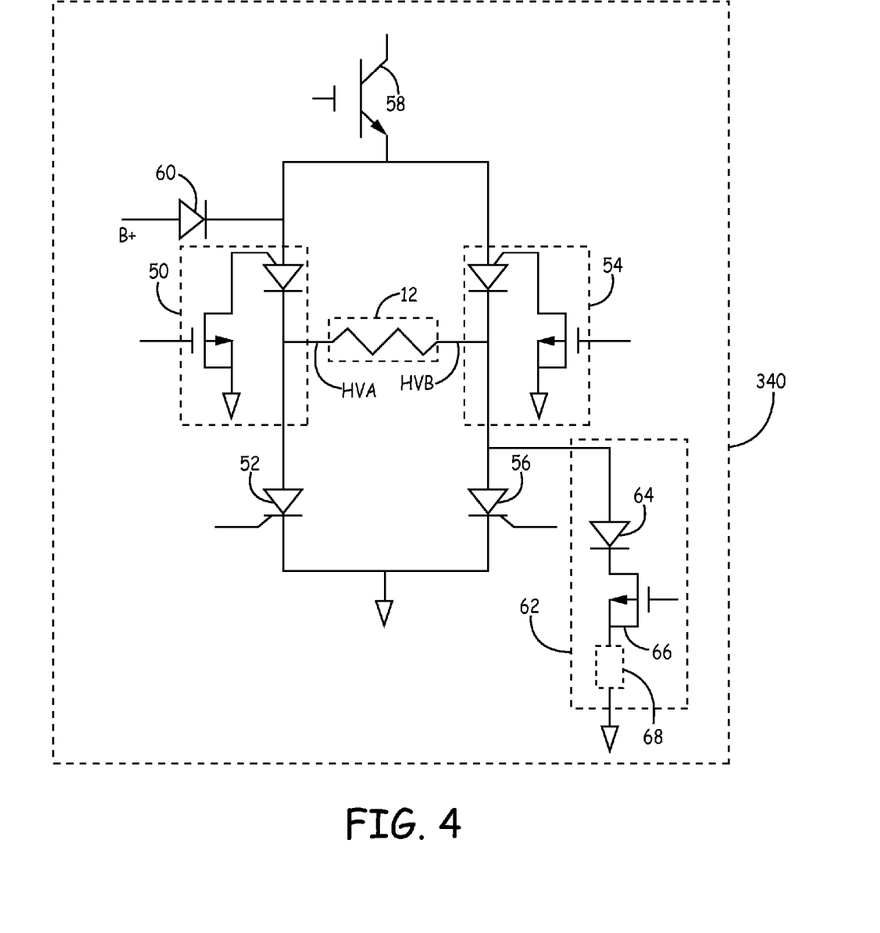
FIG. 4 illustrates an exemplary embodiment of an output circuit included in the operational circuitry of FIG. 3 in accordance with an embodiment of the present disclosure.

An exemplary embodiment of the output circuit 340 of FIG. 3 in accordance with an embodiment of the present disclosure is shown in FIG. 4. As described in reference to FIG. 3, the four output switches 50, 52, 54 and 56 allow the transfer of energy from the energy storage capacitors 356, 358, 360, and 362. Switches 50 and 54 may be provided as a series combination of semiconductor devices, such as an anode gated thyristor coupled in series with a p-channel MOSFET (FET). In such an embodiment, the FETs may be controlled by the control circuit 344 from a conducting to a non-conducting state. Switches 52 and 56 are both semiconductor switches, such as silicon controlled rectifiers (SCRs). The four output switches 50 to 56 can be switched from an off (non-conducting) to an on (conducting) condition based on control signals provided by the control circuit 344.

Switches 50 to 56 remain in a conducting state as long as the control signal provided by the control circuit 344 is present. The circuit diagram of FIG. 4 further includes a first diode 60 that has a cathode coupled to the common node connecting leg 50 to the discharge switch 58. The anode of first diode 60 is coupled to the positive high voltage battery voltage EXT B+ terminal.

Additionally, an impedance testing leg 62 may be coupled between the common node connecting the HV-B terminal to leg 56 and the common circuit ground terminal. The impedance testing leg 62 may in one embodiment include a second diode 64 coupled in series to a FET 66.

In accordance with the embodiment of FIG. 4, the addition of the diode 60 and the impedance testing leg 62 facilitates the performance of a subthreshold lead impedance test in a SubQ ICD device. The subthreshold lead impedance test may utilize energy delivered from the battery 312 that is limited to an energy value than is less than the stimulation threshold of the patient 12. The stimulation threshold value will vary from patient to patient and is typically determined during implant or shortly thereafter during the initial setup to determine an appropriate stimulation energy for the therapy delivered to the patient 12. For example, the subthreshold lead impedance test may deliver a minimum energy pulse having a current of approximately 1 mA. The current may be controlled to an accuracy threshold of about 10%-20% (of the 1 mA).

The current delivered by the minimum energy pulse may be controlled by a control signal issued through the control circuit 344. The signal issued by the control circuit 344 modulates the gate of the FET 66. In an alternative embodiment, the impedance testing leg 62 may further include a current sink 68 that is coupled in series with the FET 66. In one example, current sink 68 is a resistor. The resistor may be selected having a value that ensures a current flow that is as close as possible to the selected current for the minimum energy pulse throughout the expected range of lead impedances and battery 312 voltages. It is contemplated that whichever embodiment is utilized, a manufacturing test may be performed to calibrate the system. This calibration value may be stored in a memory location of the IMD and used to calculate the lead impedance from HV-A to HV-B.

In operation, a lead impedance measurement may be initiated by the microcomputer 342. Control signals may be issued by the control circuit 344 to bias the leg 50 in a conducting state and to bias the legs 52, 54, and 56 in a non-conducting state. The control signals additionally turn on the FET 60 to conduct current from the battery 312 to the impedance testing leg 62 through leg 50 and the HV-A, HV-B terminals that are coupled to the patient 12 through electrodes 24, 28. In the circuit schematic of FIG. 4, the patient tissue to which the electrodes 28, 28 are connected may be reflected as a load 12b. The current conducted through a test path defined by the FET 60, leg 50, and electrodes 24, 28 is returned to system ground via the impedance testing leg 62.

The lead impedance measurement is performed during portions of operation of the IMD when therapy is not being provided. In an embodiment, a control signal may also be provided to bias discharge switch 58 in a non-conducting state.

To obtain the lead impedance, a measurement of the voltage across the HV-A, HV-B terminals is performed by the amplifier circuit 378 under control of the control circuit 344 during the current conduction through the test path. The lead impedance may be calculated as a function of the current and the measured voltage. In some embodiments, the calculation of the lead impedance may take into account the calibration value to compensate for variations in the accuracy of the current control.

The techniques and technologies presented herein are intended to illustrate the functional operation of an exemplary device, and should not be construed as reflective of a specific form of software, firmware or hardware necessary to practice the invention. It is believed that the particular form of software, firmware, and hardware will be determined by the particular system architecture employed in the device or system. For example, an embodiment of a system or a component may employ various integrated circuit components, e.g., memory elements, digital signal processing elements, logic elements, look-up tables, or the like, which may carry out a variety of functions under the control of one or more microprocessors or other control devices. To the extent that there is any ambiguity or inconsistency between the text and the circuit symbols depicted in the figures, the figures will be deemed to control.

Providing software, firmware and hardware to accomplish the present invention, given the disclosure herein, is within the abilities of one of skill in the art. For the sake of brevity, conventional techniques related to ventricular/atrial pressure sensing, IMD signal processing, telemetry, and other functional aspects of the systems (and the individual operating components of the systems) may not be described in detail herein. The connecting lines shown in the various figures contained herein are intended to represent example functional relationships and/or physical couplings between the various elements. It should be noted that many alternative or additional functional relationships or physical connections may be present in an embodiment of the subject matter.

The description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although the schematics shown in the figures depict exemplary arrangements of elements, additional intervening elements, devices, features, or components may be present in an embodiment of the depicted subject matter.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

What is claimed is:

1. An implantable medical system, comprising:
   a housing;
   a lead coupled to the housing;
   a first electrode coupled at a distal end of the lead;
   a second electrode;
   an operational circuitry disposed within the housing, the operational circuitry including:
      an energy source;
      a diode electrically coupled to the energy source at a first terminal;
      an output circuit arrayed having a high side and a low side and including four interconnected legs, the high side having a first leg and a third leg and the low side having a second leg and a fourth leg, wherein the first leg is coupled between a second terminal of the diode and the first electrode and the fourth leg is coupled to the second electrode, wherein each of the four interconnected legs comprises a semiconductor device;
      an impedance testing leg coupled to the output circuit; and
      a control circuit configured to control monitoring of a voltage between the first electrode and the second electrode.

2. The implantable medical system of claim 1, wherein the impedance testing leg is coupled between the second electrode and a first terminal of the fourth leg.

3. The implantable medical system of claim 1, wherein the control circuit configures the four interconnected legs such that a testing current delivered from the energy source is directed to pass from the diode to the impedance testing leg through the first electrode and the second electrode and the control circuit monitors the voltage in response to delivery of the testing current.

4. The implantable medical system of claim 1, wherein the control circuit processes the monitored voltage to determine an impedance of the lead.

5. The implantable medical system of claim 1, wherein the control circuit is further configured to direct a testing operation including biasing the first leg and the impedance testing leg in a conducting state and delivering a testing current from the energy source through the diode to the output circuit and to the impedance testing leg, the testing current being less than a stimulus pulse voltage.

6. The implantable medical system of claim 5, wherein the control circuit closes a first switch coupled to the first leg and biases the second, third and fourth legs in a non-conducting state such that the delivered current flows between the first electrode and the second electrode.

7. The implantable medical system of claim 5, wherein the control circuit monitors the voltage between the first electrode and the second electrode triggered by the delivery of the testing current.

8. The implantable medical system of claim 5, wherein the testing current is limited to a value that is below a stimulation threshold of a patient.

9. The implantable medical system of claim 8, wherein the testing current is limited by applying current delivered from the energy source through a discrete resistor coupled in series with the diode.

10. The implantable medical system of claim 1, wherein the impedance testing leg includes a second diode coupled in series to a switch.

11. The implantable medical system of claim 1, wherein the second electrode is coupled to the housing.

12. The implantable medical system of claim 1, wherein the second electrode is coupled to a proximal end of the lead.

13. The implantable medical system of claim 1, wherein the third leg is coupled between a first terminal of the fourth leg and a first terminal of the first leg, and the second leg is coupled between a second terminal of the first leg and a second terminal of the fourth leg.

14. The implantable medical system of claim 1, further comprising:
   a capacitor coupled to the energy source; and
   a discharge switch coupled between the output circuit and the capacitor, wherein the control circuit controls the discharge switch for applying a stimulus pulse generated by the capacitor through the first electrode and the second electrode.

15. The implantable medical system of claim 14, wherein the control circuit is further configured to direct the stimulus pulse having a first polarity through one of the high side legs and one of the low side legs and to direct the stimulus pulse having a second polarity through the other of the high side legs and the other of the low side legs.

16. The implantable medical system of claim 14, wherein the control circuit is further configured to direct the stimulus pulse having a first polarity through the first leg and the fourth leg such that current passes from the first electrode to the second electrode and to direct the stimulus pulse having a second polarity through the third leg and the second leg such that current passes from the second electrode to the first electrode.

17. The implantable medical system of claim 1, wherein the first and third legs comprise anode gated thyristors (AGT) and the second and fourth legs comprise silicon controlled rectifiers (SCR).

18. The implantable medical system of claim 1, wherein the first electrode and the second electrode are configured to be connected to a patient.

19. The implantable medical system of claim 1, further comprising an amplifier circuit, wherein the control circuit issues a control signal to the amplifier circuit to enable monitoring of the voltage between the first electrode and the second electrode.

20. An implantable medical system, comprising:
- a housing;
- a lead coupled to the housing;
- a first electrode coupled at a distal end of the lead;
- a second electrode;
- an operational circuitry disposed within the housing, the operational circuitry including:
  - an energy source;
  - a diode electrically coupled to the energy source at a first terminal;
  - an output circuit arrayed having a high side and a low side and including four interconnected legs, the high side having a first leg and a third leg and the low side having a second leg and a fourth leg, wherein the first leg is coupled between a second terminal of the diode and the first electrode and the fourth leg is coupled to the second electrode;
  - an impedance testing leg coupled to the output circuit; and
  - a control circuit configured to control monitoring of a voltage between the first electrode and the second electrode, wherein the control circuit is further configured to direct a testing operation including biasing the first leg and the impedance testing leg in a conducting state and delivering a testing current from the energy source through the diode to the output circuit and to the impedance testing leg, the testing current being less than a stimulus pulse voltage, wherein the testing current is limited to a value that is below a stimulation threshold of a patient, and wherein the impedance testing leg includes a semiconductor switch and the control circuit modulates a gate of the switch to limit the testing current.

\* \* \* \* \*